United States Patent [19]

Brasey

[11] Patent Number: 4,707,360

[45] Date of Patent: Nov. 17, 1987

[54] VASCULOPROTECTING PHARMACEUTICAL COMPOSITIONS

[75] Inventor: Pierre-Noel Brasey, Geneva, Switzerland

[73] Assignee: Seuref A.G., Vaduz, Liechtenstein

[21] Appl. No.: 857,152

[22] Filed: Apr. 29, 1986

[30] Foreign Application Priority Data

Apr. 30, 1985 [CH] Switzerland ............... 1826/85

[51] Int. Cl.$^4$ ............... A61K 37/48; A61K 31/70; A61K 31/35
[52] U.S. Cl. ............... 424/94.1; 514/25; 514/27; 514/456; 424/DIG. 15
[58] Field of Search ............ 424/94.1, DIG. 15, 94; 514/25, 27, 456

[56] References Cited

PUBLICATIONS

Merck Index, 9th ed. Nos. 1240, and 9496, 1976.

*Primary Examiner*—J. R. Brown
*Assistant Examiner*—John W. Rollins, Jr.
*Attorney, Agent, or Firm*—Bucknam and Archer

[57] ABSTRACT

Pharmaceutical compositions having vasculoprotecting activity, containing an ubiquinone compound together with one or more compounds of flavanoid, heparinoid, terpenic or glycosidic structure, such as escin, troxerutin, asiaticoside, heparin, delphinidin, tribenoside.

2 Claims, No Drawings

VASCULOPROTECTING PHARMACEUTICAL COMPOSITIONS

The present invention relates to pharmaceutical compositions containing as the active ingredient one ubiquinone compound together with known compounds suitable for vascular therapy.

Examples of said vasculoprotecting compounds are those having flavonoid, terpenic, glycosidic, heparinoid structures, such as escin, rutin, troxerutin, diosmin, asiaticoside, hesperidin, tribenoside, etc.

The components of the compositions according to the invention display a synergistic action on the regulation of vascular activity and permeability.

Moreover, said compositions prevent trophic and metabolic tissular changes as well as those from anoxic conditions, due to impaired vascularization.

Among the vasculoprotecting agents, particularly known are flavonoids, whose effectiveness as capillary-protecting agents, antiedemics and cicatrizants in vasal diseases has been widely described in literature (Bohr D. F.—J. Pharmacol. Exp. Ther., 97-243-1949; Gugler R.—Ges. Arch. Exp. Pathol. Pharm.—274-R45-1972; Haeger K.—Zbl. Phlebol., 6-526-1967; Rozkoch K.—Europ. J. Clin. Pharmacol., 3-243-1971; Allen S.—Practioner, 205-221-1970).

Similar activities were disclosed for heparin and heparinoids (Witte S., Thromb. Diath. Hemorrhag., 2-146-1958; Jacques L. B.—Ann. N.Y. Acad. Sci., 115-781-1969; Nicolaides A. N.—Lancet, 2-890-1972).

All the flavonoids, at the vasal level, act to regulate the entry of calcium into the cells (Ludwig O.—Med. Welt, 16-1181-1942) and to inhibit any increased effect of lysosomial enzymes, related to pathological conditions (Niches P.—Angiologica, 8-297-1971).

Moreover, it should be pointed out that the synthesis of glycosaminoglycans, which are among the main components of vasal wall and control its hydropexic action as well as ion passage, takes place mainly by activation of Golgi apparatus, whose function is conditioned by the availability of respiratory chain, related to Coenzyme $Q_{10}$ (Balasz E.—Arthritis-Arthrose Verlag Haan Huber, Bern Wien, 46-1971; Crane F. L.—"Biomedical and Clinical Aspects of Coenzyme Q", Folkers K. Ed., Vol. 1, Elsevier Amsterdam, 1977, p, 3; Lenaz G.—Drugs Exptl. Clin. Res., 10-481-1984).

A deficiency in oxygen diffusion and utilization, as well as tissular hypoxic conditions, have been also indicated as causes of vascular diseases and atherosclerosis (Robertson A. L.—Progr. Biochem. Pharmacol., Vol. 4, p. 305, Karger, Basel, 1968; Zempleny T.—Symposia Angiologica Santoriana—4 Int. Symp., Fribourg-Nyon 1972—Angiologica, 9-429-1972).

Coenzyme $Q_{10}$ is known to control the transport of mytochondrial electrons, and consequently to play a role in oxygen utilization and tissue metabolism, since tissular and cellular energetic processes are related to hydrogenion transport (Morton R. A.—Nature, 182-1764-1958; Gale P. H.—Arch. Biochem. Biophys., 93-211-1961).

In fact, Coenzyme $Q_{10}$ avoids the damages caused by cellular lypoperoxydation, intracellular calcium increase and lysosomial enzyme release, which markedly affect normal cellular and tissular vasal functioning (Lehedev A. V.—J. Mol. Cell. Cardiol., 14 (Suppl. 3) 99-1982; Littarru G. P.—Drugs Exptl. Clin. Res., 10-491-1984).

Now it has surprisingly been found that ubiquinone compounds, particularly Coenzyme $Q_{10}$, synergistically enhance the activity of known vasculoprotecting agents, particularly chalones, aurones, flavones, flavanones, flavanols, flavanonols, flavanediols, leukoanthocyanidines, cumarins, hesperidins, catechins, anthocyanidines, natural or semisynthetic derivatives thereof, or vegetal extracts containing them.

By means of the combination of the present invention, a marked increase in therapeutic action is obtained, in comparison with the one of the single components, without toxic or side-effects.

The pharmaco-toxycologic tests carried out will be hereinafter described, in order to illustrate the advantages of the compositions of the present invention.

Coenzyme $Q_{10}$ is known to have a low toxicity, its $DL_{50}$ in rats and mice being respectively higher than 500 and 250 mg/kg by intraperitoneal administration, and higher than 4 g/kg by subcutaneous administration.

Flavonoids and heparinoids are also known to be little toxic, and the combination thereof with Coenzyme $Q_{10}$ shows no changes in the toxicity values of the components. 1:1 Combination of Coenzyme $Q_{10}$ and anthocyanine, hydroxyethylrutoside or catechin, showed $DL_{50}$ values higher than 1 g/kg in both rats and mice, by oral administration.

Also the chronic toxicity tests carried out in the rat by oral daily administration of the above combinations in 1:1 ratio for 30 consecutive days showed no pathologic changes in the body weight and in hemathological and biochemical parameters.

On the contrary, the above combinations proved to be surprisingly effective in different pharmacological tests, such as wound-healing time in experimental wounds in the rabbit, rupture resistance of cicatrices in the mouse, antiedemic activitiy in the rat, activity on capillary permeability and ergotamine arteritis in the rat.

In all the above tests a marked synergism between Coenzyme $Q_{10}$ and the other vasoprotecting compounds was evidenced, the obtained results being surprisingly more favourable than the ones obtained using the single components.

The tests were carried out combining Coenzyme $Q_{10}$ with O-($\beta$-hydroxyethylrutoside), escin (a saponin from Esculus hippocastanum), tribenoside (ethyl 3,5,6-tri-O-benzyl-$\delta$-glycofuronoside), delphinidin (anthocyanidin), and total extract of Centella asiatica (asiaticoside).

The tests on wound healing activity of the compositions of the invention were carried out on cutaneous wounds in the rat orally treated with prednisolone, according to the procedure of J. J. Morton (Morton J. J. P., Malone M. H.—Arch. Int. Pharmacodyn., 196-117-1972).

The cicatrization of the cutis of the back of the rat previously scarified was delayed by oral treatment with 0.25 mg/kg of prednisolone.

The test composition was applied on the wound, after appropriate suspension at different concentrations.

The area of the wound on the third day of treatment was measured: the results reported in the following Table 1 evidence a marked synergistic action of the compositions of the invention.

TABLE 1

| Compound | Dose mg/cm² cutis | % Reduction |
| --- | --- | --- |
| A | 100 | 22 |

TABLE 1-continued

| Compound | Dose mg/cm² cutis | % Reduction |
|---|---|---|
| B | 10 | 15 |
| C | 50 | 11 |
| D | 25 | 18 |
| E | 25 | 12 |
| A + B | 100 + 10 | 65 |
| A + C | 100 + 50 | 40 |
| A + D | 100 + 25 | 56 |
| A + E | 100 + 25 | 63 |

A = Coenzyme $Q_{10}$
B = Delphinidin
C = Escin
D = Tribenoside
E = Asiaticoside.

Oral administration of the compositions of the invention also surprisingly increased the rupture resistance of scars induced in the mouse by incision of cutis of the back. The treatment was continued during 3 consecutive days after surgical suturation of the wound, after this period the cutis portion containing the scar was removed, one end thereof was fixed to a support and the other one was subjected to continuous traction (110 g/minute). The rupture strength results are reported in Table 2 hereinbelow.

TABLE 2

| Compound | Dose mg/kg (per os) | % Rupture resistance (in grams) |
|---|---|---|
| A | 25 | 19 |
| B | 100 | 21 |
| C | 25 | 16 |
| D | 50 | 15 |
| E | 25 | 13 |
| A + B | 25 + 100 | 75 |
| A + C | 25 + 25 | 82 |
| A + D | 25 + 50 | 80 |
| A + E | 25 + 25 | 95 |

A, B, C, D, E = vide Table 1.

The capillary resistance tests were carried out according to the procedure of Charlier R. (Charlier R., Hosslet A., Colot M.—Arch. Int. Physiol. Biochem., 71-1-1963), by oral treatment for 3 consecutive days of rats, previously feeded for 2 weeks with a diet lacking in vitamin P.

The increase of capillary resistance was measured by means of a mercury vacuometer.

The results are reported in following Table 3.

TABLE 3

| Compound | Dose mg/kg (per os) | Capillary resistance % increase |
|---|---|---|
| A | 25 | 2.5 |
| B | 100 | 12.2 |
| C | 25 | 9.5 |
| D | 50 | 12.9 |
| F | 50 | 11.5 |
| A + B | 25 + 100 | 35.5 |
| A + C | 25 + 25 | 24.3 |
| A + D | 25 + 50 | 32.4 |
| A + F | 25 + 50 | 25.5 |

A to D = vide Table 1.
F = Hydroxyethylrutoside.

Also in this test a marked synergetic action was evidenced.

The pharmacological compositions of the invention may be prepared according to conventional procedures of pharmaceutical technique, using pharmaceutically acceptable carriers or diluents.

Non-limiting examples of suitable compositions of the invention are reported hereinbelow.

TABLETS

Coenzyme $Q_{10}$ 10 mg+escin 20 mg
Coenzyme $Q_{10}$ 50 mg+escin 20 mg
Coenzyme $Q_{10}$ 10 mg+hydroxyethylrutoside 300 mg
Coenzyme $Q_{10}$ 50 mg+hydroxyethylrutoside 500 mg
Coenzyme $Q_{10}$ 10 mg+asiaticoside 10 mg
Coenzyme $Q_{10}$ 50 mg+asiaticoside 10 mg
Coenzyme $Q_{10}$ 10 mg+tribenoside 400 mg
Coenzyme $Q_{10}$ 50 mg+tribenoside 500 mg
Coenzyme $Q_{10}$ 10 mg+delphinidin 100 mg
Coenzyme $Q_{10}$ 50 mg+delphinidin 200 mg.

SUGAR-COATED PILLS

Coenzyme $Q_{10}$ 10 mg+escin 20 mg
Coenzyme $Q_{10}$ 50 mg+hydroxyethylrutoside 500 mg
Coenzyme $Q_{10}$ 10 mg+tribenoside 500 mg
Coenzyme $Q_{10}$ 50 mg+tribenoside 500 mg

CAPSULES

Coenzyme $Q_{10}$ 10 mg+escin 20 mg
Coenzyme $Q_{10}$ 10 mg+tribenoside 400 mg
Coenzyme $Q_{10}$ 50 mg+tribenoside 500 mg

CREAMS

Coenzyme $Q_{10}$ 1%+escin 1%
Coenzyme $Q_{10}$ 1%+hydroxyethylrutoside 2%
Coenzyme $Q_{10}$ 1%+asiaticoside 1%
Coenzyme $Q_{10}$ 1%+tribenoside 1%
Coenzyme $Q_{10}$ 1%+delphinidin 1%.

OINTMENTS

Coenzyme $Q_{10}$ 1%+escin 1%
Coenzyme $Q_{10}$ 1%+sodium heparin 10,000 IU/100 g of ointment
Coenzyme $Q_{10}$ 1%+natural heparinoid 70,000 IU/g
Coenzyme $Q_{10}$ 1%+sulfate glucuronylglycosaminoglicane(heparinoid) 200 mg, equal to 400 UHC.

SUPPOSITORIES

Coenzyme $Q_{10}$ 50 mg+escin 50 mg
Coenzyme $Q_{10}$ 100 mg+hydroxyethylrutoside 500 mg
Coenzyme $Q_{10}$ 50 mg+total extract of Centella asiatica (equal to 10 mg of asiaticoside) 50 mg
Coenzyme $Q_{10}$ 100 mg+tribenoside 1,000 mg
Coenzyme $Q_{10}$ 100 mg+delphinidin 400 mg.

The compositions of the invention will be administered 2 to 4 times daily, even for prolonged treatment, at dosages depending on age, weight and general conditions of the patient.

I claim:

1. A pharmaceutical composition having vasculoprotecting activity, containing as the active ingredients component (a) which is coenzyme $Q_{10}$ and component (b) which is a member selected from the group consisting of delphinidin, asiaticoside, escin, tribenoside and O-(β-hydroxyethylrutoside) in the ratios between 10:1 and 1:4 of said component (a) to component (b).

2. The pharmaceutical composition according to claim 1 in the form of capsules, tablets, syrups, granulates, sterile solutions, ointments, creams, lotions, gels or suppositories for oral, parenteral, rectal or topical administration.

* * * * *